(12) United States Patent
Naredo

(10) Patent No.: US 6,601,699 B1
(45) Date of Patent: Aug. 5, 2003

(54) ANTISEPTIC TOOTHBRUSH SOAK SYSTEM

(76) Inventor: David Naredo, 505 Elm, Kerrville, TX (US) 78028

( * ) Notice: Subject to any disclaimer, the term of this patent is extended or adjusted under 35 U.S.C. 154(b) by 20 days.

(21) Appl. No.: 10/011,758

(22) Filed: Dec. 11, 2001

Related U.S. Application Data
(60) Provisional application No. 60/292,955, filed on May 24, 2001.

(51) Int. Cl.7 .............................................. B65D 81/24
(52) U.S. Cl. .................................. 206/209.1; 206/362.1
(58) Field of Search ................................ 206/207, 209, 206/209.1, 361, 362, 362.1, 362.2, 15.2, 15.3, 368, 369

(56) References Cited

U.S. PATENT DOCUMENTS

| | | | |
|---|---|---|---|
| 1,278,789 A | * 9/1918 | Thompson | 206/209.1 |
| 1,743,646 A | * 1/1930 | Alderman, Jr. | 206/209.1 |
| 2,280,431 A | 4/1942 | Hart | |
| 2,584,042 A | * 1/1952 | Ober | 206/209.1 |
| 3,881,868 A | 5/1975 | Duke | |
| 3,884,635 A | * 5/1975 | Sloan | 206/209.1 |
| 3,904,362 A | 9/1975 | DePaolo | |
| 4,214,657 A | * 7/1980 | Winston | 206/209.1 |
| 4,880,020 A | * 11/1989 | Schurgin | 132/308 |
| 4,915,219 A | * 4/1990 | Ottimo | 206/209.1 |
| 4,997,629 A | * 3/1991 | Marchand et al. | 422/300 |
| D337,206 S | * 7/1993 | Crawford | D4/199 |
| 5,566,823 A | 10/1996 | Summers | |
| 5,690,214 A | * 11/1997 | Gaines et al. | 206/209.1 |
| 5,882,613 A | * 3/1999 | Gipson, II | 422/300 |
| 6,119,854 A | * 9/2000 | Prentice et al. | 206/209.1 |
| 6,360,884 B1 | * 3/2002 | Smith et al. | 206/209.1 |

* cited by examiner

*Primary Examiner*—Shian Luong
(74) *Attorney, Agent, or Firm*—Patent & Trademark Services; Thomas Zack; Joseph H. McGlynn

(57) ABSTRACT

A system for both holding a toothbrush and permitting the flow of an antiseptic solution from a container to the holder for the toothbrush.

9 Claims, 2 Drawing Sheets

ANTISEPTIC TOOTHBRUSH SOAK SYSTEM

This invention claims the benefit of the U.S. Provisional application 60/292,955 filed on May 24, 2001.

BACKGROUND OF THE INVENTION

The present invention relates to a holder for a toothbrush with an antiseptic solution holder.

Holders for toothbrushes are known. It is also well known that the mouths of persons naturally contain a considerable amount of bacteria and other pathogens. Therefore, it is very desirable that a used toothbrush be kept as clean as possible prior to its reuse. To do so, it has been proposed that the stored toothbrush be kept in a sterile condition. At least one previous invention provides for a toothbrush holder that cleans and sterilizes one or more brushes while they are supported and enclosed in the holder.

DESCRIPTION OF THE PRIOR ART

Toothbrush holders which contain antiseptic solutions along with one or more toothbrushes are known to the prior art. For example, U.S. Pat. No. 2,280,431 to Hart discloses a toothbrush holder which cleans and sterilizes the brushes while they are supported and enclosed in the holder.

U.S. Pat. No. 3,881,868 to Duke discloses a toothbrush holder which has a built in reservoir for holding an antiseptic solution.

U.S. Pat. No. 3,904,362 to DePaolo discloses a toothbrush holder which has a plurality of compartments to both hold and sterilize toothbrushes.

U.S. Pat. No. 5,566,823 to Summers discloses a toothbrush holder in a tray with a plurality of compartments to hold and sterilize toothbrushes.

In the present invention a toothbrush soaking system has a valve mechanism associated with a container of an antiseptic solution and a holder for at least one toothbrush with a hinged lid to hold the toothbrush and the reservoir of antiseptic solution, which communicates with the toothbrush holder, all as will be detailed in the specification that follows hereafter.

SUMMARY OF THE INVENTION

This invention relates to a system for both holding a toothbrush and permitting the flow of an antiseptic solution from a container or reservoir to the holder for the toothbrush.

It is the primary object of the present invention to provide for an improved system which holds a toothbrush and can dispense an antiseptic solution from a container to the toothbrush holder.

Another object is to provide for such a system having a flow control valve between the container and the holder for the toothbrush.

These and other objects and advantages of the present invention will become apparent to readers from a consideration of the ensuing description and the accompanying drawings.

DESCRIPTION OF THE PREFERRED EMBODIMENT

Figures 1, 2:
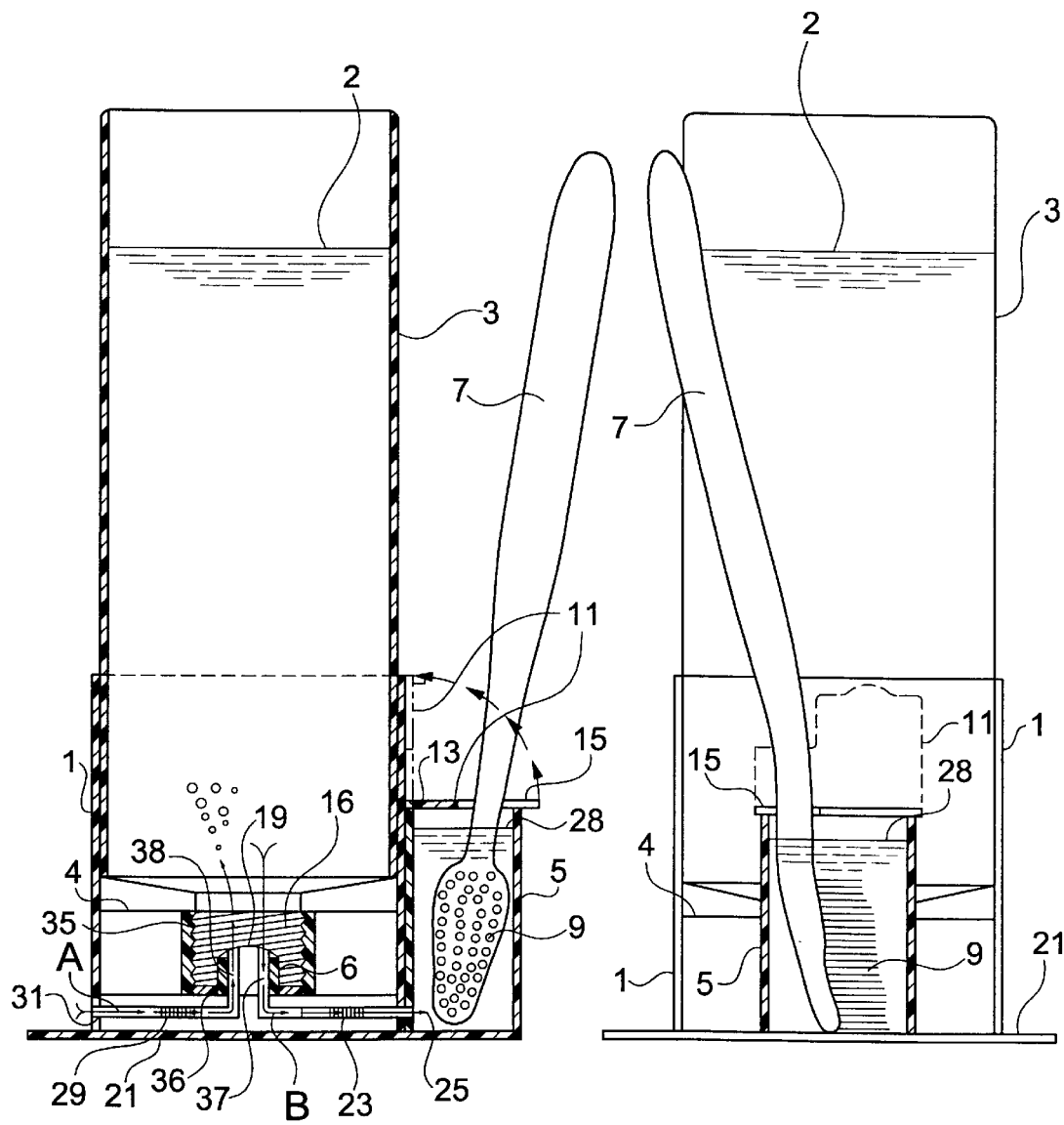
FIG. 1 is a cross sectional view of the holder used in the system forming the present invention.
FIG. 2 is side view of the FIG. 1 system showing the toothbrush holder.

FIG. 1 is a cross sectional view of the two holders 1 and 5 used in the system forming the present invention. The front facing wall of each holder has been removed to show the internal contents of the holders. The supply holder 1 is used to hold the container 3, which has an antiseptic solution 2 contained therein. Mounted to the supply holder 1, by any conventional means, is the toothbrush holder 5 which holds a conventional toothbrush 7, with its bristle or brushing end 9 oriented within the dispensed solution 2 from the container 3. At the top of the toothbrush holder 5 a lid 11 has a hinge 13. This lid 11 acts to retain and protect the toothbrush within the toothbrush holder 5. The lid 11 has an opening 15 to permit the handle of the toothbrush to extend out of the toothbrush holder 5. When it is desired to use the toothbrush or to empty the solution 2 within the toothbrush holder 5, the lid 11 is pivoted upwardly, as shown by the dotted lines in FIG. 1, and the toothbrush 7 is removed by simply lifting the toothbrush upwardly. If the solution 2 is to be discarded, both holders 1, 5 are raised and tilted with the lid 11 opened to discharge the solution to an appropriate location, like a sink.

The antiseptic solution container 3 is designed to fit snugly, yet able to turn, into the open top of the supply holder 1. A threaded connection 16, which normally retains a removable end cap for the antiseptic container 3, can also be used to secure the end of the container 3 to the bottom of the supply holder 1. This can be accomplished by threading the connector 16 into a mating connector 35. If desired, a ring seal 6 could be used around a pointed projection 19 to insure a leak free fit. Four spokes 4 hold the connector 35 to the outer walls of supply holder 1 for additional support.

Normally, containers such as 3 will have a safety seal 36 attached to the end of the container 3. In order to puncture this seal, the pointed projection 19 is provided in the base of the supply holder 1. Once the seal is punctured by the projection 19, fluid 2 within the container 3 can be introduced into the bottom of the supply holder 1. An internal passageway 37 in the projection 19 and the base of the supply holder 1 allows the fluid 2 to pass into toothbrush holder 5. A spring biased valve 23 is placed near the bottom of the supply holder 1. The valve 23 normally blocks the passage 25 between the supply holder 1 and the toothbrush holder 5. The user can squeeze the plastic container 3, which will increase the fluid pressure and open the valve 23. As long as the pressure within the container 3 is sufficient, the fluid will flow to the toothbrush holder 5 until it reaches a predetermined level 28. Once the fluid builds up to level 28 in toothbrush holder 5, it completely covers the brushing surface or head 9 of the toothbrush 7.

Another spring biased valve 29 is also positioned near the bottom of supply holder 1, and normally controls the entry of external air into container 3 from an external orifice 31 through passageway 38. Valve 29 is activated when container 3 is released after being squeezed creating a vacuum within container 3. Ambient air flows into the chamber in the direction of arrows A. The flow of the fluids from container 3 to holder 5 is shown by arrow B.

FIG. 2 is a side view of the FIG. 1 system taken at ninety degrees from FIG. 1 showing the toothbrush holder 5 in relation to the container 3. In this view the front wall of holder 5 has been removed. Normally, the two holders 1 and 5 are molded together as a unitary structure with both holders being joined to the common base 21. However, the holders 1 and 5 could be made as separate pieces and then be joined together by any conventional means. The top door or lid 11 (shown in dotted line format when opened) has an opening 15, which closely covers the stem of the inserted toothbrush 7, and is used to protect the end 9 from foreign particles, which might enter the holder 5. The edge of the lid 11, surrounding the opening for the toothbrush 15, might have a soft material that would cover any open areas between the toothbrush stem and the lid 11 when closed.

Figure 3:
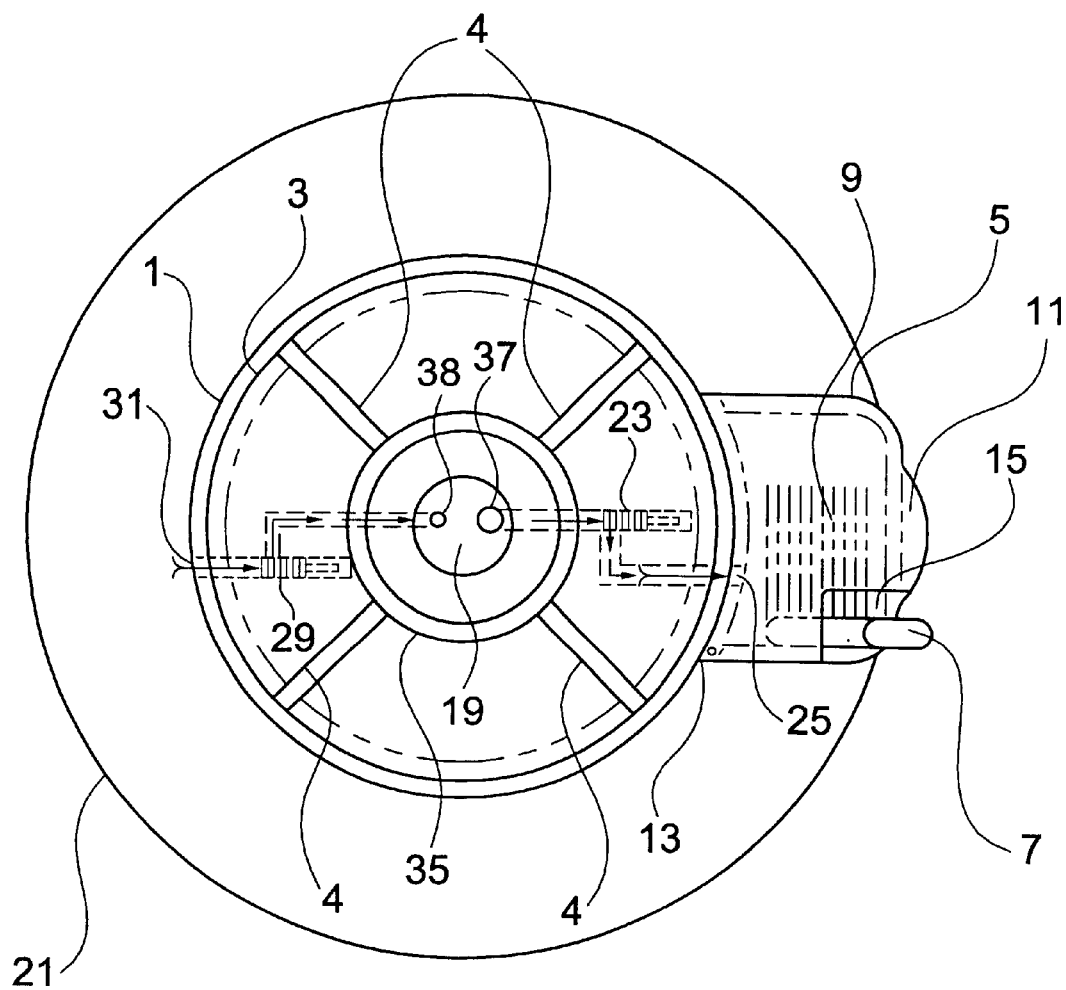
FIG. 3 is a top view of the FIG. 1 system.

FIG. 3 is a top view of the FIG. 1 system. The common base 21, for both holders 1, 5, is circular, although other shapes could be used, and this base extends under the toothbrush holder 5. The lower supply holder 1 is configured the same as the inserted container 3 for the antiseptic solution which is also shown as circular. The toothbrush holder 5 is generally rectangular with the side against the holder 1 being shaped to match the outside surface of holder 1. Matching the shape of one side of toothbrush holder 5 to holder 1 will help to prevent leaks but is not necessary if the passageway 37 and orifice 25 are extended under holder 5 with orifice 25 entering from the bottom of holder 5 rather than from the side. Bracing will still be required between holder 1 and toothbrush holder 5 by extending the sides of the toothbrush holder 5 to attach to the holder 1. As is apparent from this view, the door or lid I 1 substantially covers the top surface of holder 5 except for the small opening 15 used to accommodate the stem of the toothbrush 7. The bristles 9 of the toothbrush are shown in dotted line format, with the upwardly facing stem of toothbrush 7 being visible. The lid 11 has a small overhang which extends over the front of the toothbrush holder 5 that can be used for opening the lid 11. The ambient air and fluid flow passageways 25, 31 with their spring valves 23, 29 are also shown in dotted line format.

It should be clear that the above described present invention is designed to keep the head or brushing surface of a toothbrush free of dirt, dust, bacteria, germs, pests or other pathogens. The antiseptic solution, in which this head rests, completely covers the head while the hinged lid provides additional physical protection from particles and other solid materials. Adding a soft liner at the opening may help to accommodate different size stems and create a tighter fit overall.

Squeezing the sides of the flexible antiseptic container, when inserted into its holder, provides fluid pressure to the lower chamber of the holder after the container safety seal has been broken. One container holder valve is activated by the fluid pressure, in the antiseptic solution bottle, to permit the flow of fluid into the toothbrush holder through a communicating orifice. The other container holder valve is activated by a vacuum in the antiseptic solution bottle allowing ambient air into the bottle through the holder it is connected to. Excess solution in the toothbrush holder can be removed by tipping the whole system and pouring it out. Replacement of the solution container is a matter of unscrewing the empty container and screwing in a new replacement. The safety seal is automatically broken when the new bottle is screwed into the base.

Also, it should be understood that while only one toothbrush is shown in the holder, more than one toothbrush could be used in the present invention. Also, additional holders may be provided for holding multiple toothbrushes.

Although the preferred embodiment of the present invention and the method of using the same has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What is claimed is:

1. A toothbrush holder adapted to receive a toothbrush having a tooth brushing end, said toothbrush holder comprising;
   a holder,
   said holder having a lid hinged to the holder, and
   a container for holding an antiseptic,
   said container having a reservoir with means for controlling the supply of the antiseptic to the holder.

2. The toothbrush holder as claimed in claim 1, wherein said holder is adjacent to and fixed to the container.

3. The toothbrush holder as claimed in claim 2, in combination with an antiseptic, and
   wherein the antiseptic is a solution within the reservoir of the container, and
   said container being in fluid communication with the holder through a wall of the holder.

4. The toothbrush holder as claimed in claim 3, wherein the lid for the holder may be raised and lowered,
   said lid having an opening to receive a portion of the toothbrush when the lid is lowered.

5. The toothbrush holder as claimed in claim 4, wherein said means for controlling the supply of the antiseptic to the holder is a valve mechanism which includes a valve biased to a closed position, and which is opened by pressurized antiseptic solution.

6. The toothbrush holder as claimed in claim 1, wherein said holder and said means for holding a tooth brushing end of a toothbrush in said liquid are joined by a common base.

7. The toothbrush holder as claimed in claim 6, wherein said liquid in said container is replaced with ambient air when a vacuum is created within said container.

8. The toothbrush holder as claimed in claim 1, wherein said container and said holder are in fluid communication with each other.

9. The toothbrush holder as claimed in claim 8, wherein said fluid communication is controlled by creating pressure In said container.

* * * * *